(12) United States Patent
Aulombard et al.

(10) Patent No.: US 7,947,842 B2
(45) Date of Patent: May 24, 2011

(54) HYDRATES OF ALKALINE-EARTH SALTS OF IRBESARTAN AND THE PREPARATION THEREOF

(75) Inventors: Alain Aulombard, Lattes (FR); Philippe Mercey, Valflaunes (FR)

(73) Assignee: Sanofi-Aventis, Paris (FR)

( * ) Notice: Subject to any disclaimer, the term of this patent is extended or adjusted under 35 U.S.C. 154(b) by 139 days.

(21) Appl. No.: 11/950,555

(22) Filed: Dec. 5, 2007

(65) Prior Publication Data

US 2008/0096944 A1    Apr. 24, 2008

Related U.S. Application Data

(63) Continuation of application No. PCT/FR2006/001267, filed on Jun. 6, 2006.

(30) Foreign Application Priority Data

Jun. 6, 2005 (FR) ..................... 05 05755

(51) Int. Cl.
*C07D 257/06* (2006.01)
(52) U.S. Cl. ...................................................... 548/252
(58) Field of Classification Search .................. 548/252
See application file for complete search history.

(56) References Cited

U.S. PATENT DOCUMENTS 5,541,209 A    7/1996   Spinale et al.

FOREIGN PATENT DOCUMENTS

| WO | WO 02/06253 | 1/2002 |
| WO | WO 2006011859 A2 * | 2/2006 |

* cited by examiner

*Primary Examiner* — Shawquia Young
(74) *Attorney, Agent, or Firm* — James W. Bolcsak

(57) ABSTRACT

The invention relates to hydrates of pharmaceutically acceptable alkaline-earth salts of irbesartan and to their preparation in an aqueous medium.

7 Claims, 2 Drawing Sheets

HYDRATES OF ALKALINE-EARTH SALTS OF IRBESARTAN AND THE PREPARATION THEREOF

A subject-matter of the present invention is hydrates of the alkaline earth metal salts of irbesartan and their preparation.

Irbesartan is an antagonist of angiotensin II $AT_1$ receptors which are sold as antihypertensive and in the treatment of diabetic nephropathy.

Irbesartan, the chemical name of which is 2-(n-butyl)-3-[(2'-(1H-tetrazol-5-yl)biphenyl-4-yl)methyl]-1,3-diazaspiro[4.4]non-1-en-4-one, of formula:

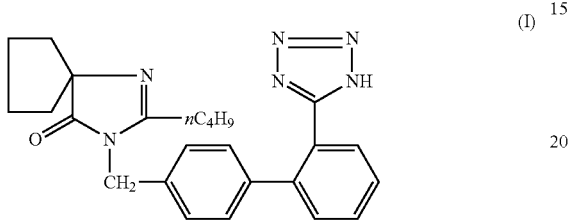

(I)

is disclosed in patent EP 454 511 B. In this patent, the salts with organic or inorganic bases, for example the salts with alkali metals or alkaline earth metals, are cited and the preparation of the potassium salt of irbesartan in organic solvents is specifically described.

Salts of irbesartan with an inorganic acid, namely the hydrobromide, the hydrochloride and the sulphate, are mentioned in U.S. Pat. No. 6,162,922 and its European equivalent EP 1 060 165 B.

Patent EP 708 103 B discloses 2 tautomeric forms of irbesartan: form A and form B. This patent indicates that form A exists in the form of stable non-hygroscopic needles which are highly electrostatic. Furthermore, a novel crystal habit of irbesartan form A is disclosed in Patent EP 1 089 994; in this patent, mention is made that the crystals of irbesartan form A with the needle habit are difficult to filter and to dry and exhibit poor flowability.

Hydrates of the alkaline earth metal salts of irbesartan which are pharmaceutically acceptable have now been found which can be easily obtained from a process the stages of which are carried out in aqueous solution. They are hydrates of the calcium salt and of the magnesium salt of irbesartan, more particularly the tetrahydrate of the calcium salt of irbesartan and the tetrahydrate of the magnesium salt of irbesartan.

Thus, a subject-matter of the present invention is the hydrates of pharmaceutically acceptable alkaline earth metal salts of irbesartan, namely: the calcium and magnesium salts of irbesartan; the present invention relates in particular to the tetrahydrate of the calcium salt of irbesartan, to the tetrahydrate of the magnesium salt of irbesartan, and more particularly to the crystalline forms of these compounds.

The salts according to the present invention are prepared by a process characterized in that:
- a sodium salt of irbesartan is prepared in aqueous solution; then
- the sodium salt of irbesartan is displaced by the desired alkaline earth metal salt in aqueous medium.

The hydrate of the alkaline earth metal salt of irbesartan thus formed is isolated by filtration; it is subsequently dried.

Thus, the 2 stages of the process according to the invention are carried out in aqueous medium, which exhibits numerous advantages:
- absence of residual solvents and thus reduction in the costs and absence of environmental problems;
- possibility of sterilizing the aqueous solutions in the 2 stages of the process;
- controlled crystallization of the salt formed;
- ease of filtration and of drying of the salt obtained;
- absence of electrostatic behaviour of the salt obtained and ready tabletting.

Figure 1:
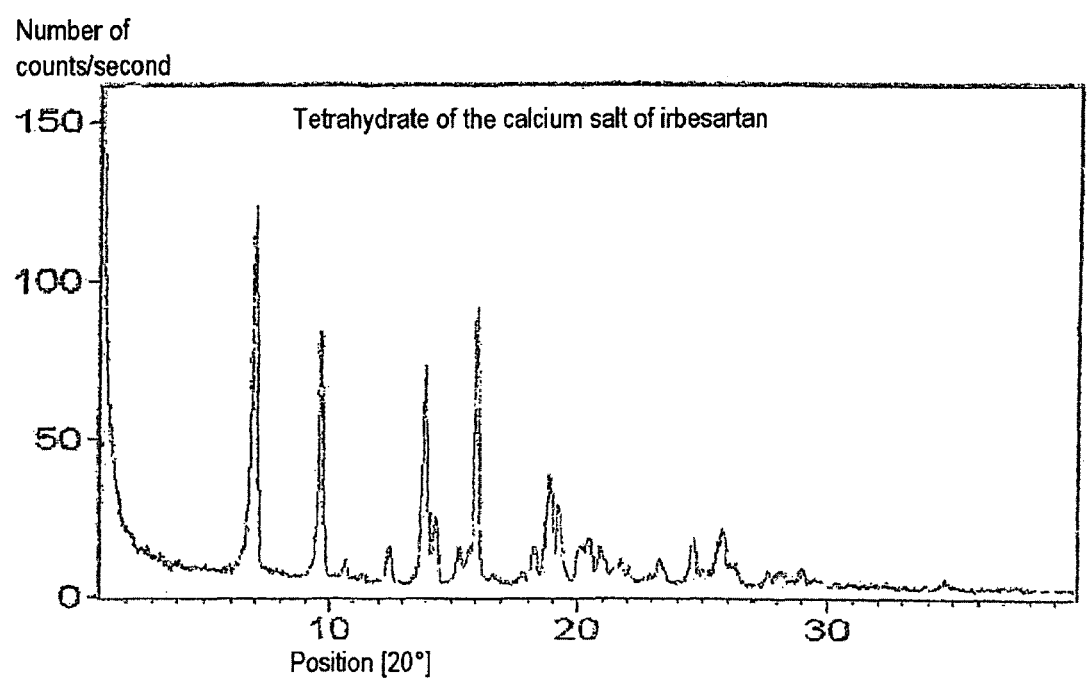
FIG. 1 shows the x-ray diffraction results for the tetrahydrate of the calcium salt of irbesartan.

The X-ray powder diffractograms were recorded for the crystalline forms of the tetrahydrate of the calcium salt of irbesartan and of the tetrahydrate of the magnesium salt of irbesartan. The X-ray diffraction profile of the powder (diffraction angle) was determined with a Philips X'pert (θ/θ) diffractometer, Bragg-Brentano type; source $CuK\alpha_1$, $\lambda=1.5406$ Å; scanning range 2° to 40° at 1° per minute in Bragg 2θ.

It is found that the powder diagrams of the tetrahydrate of the calcium salt of irbesartan and of the tetrahydrate of the magnesium salt of irbesartan are virtually identical.

The lines characteristic of the powder diffractograms of the 2 compounds are listed in the following table:

| Peak Angstrom | Angle 2θ° |
| --- | --- |
| 12.62765 | 7 |
| 9.30946 | 9.5 |
| 8.50577 | 10.4 |
| 7.08112 | 12.5 |
| 6.41684 | 13.8 |
| 6.32562 | 14 |
| 5.64430 | 15.7 |
| 5.53914 | 16 |
| 4.82170 | 18.4 |
| 4.72000 | 18.8 |

The parameters of the crystal unit cell were determined for each of the salts from their powder diffractograms

Tetrahydrate of the Magnesium Salt of Irbesartan

| | Distance (Å) | | Angles (°) |
| --- | --- | --- | --- |
| a | 18.17 ± 0.02 | α | 90 |
| b | 18.60 ± 0.02 | β | 106.89 |
| c | 17.49 ± 0.02 | γ | 90 |

Unit cell volume: 5655.3 Å$^3$
Å means angstrom

Tetrahydrate of the Calcium Salt of Irbesartan

| | Distance (Å) | | Angles (°) |
|---|---|---|---|
| a | 17.86 ± 0.04 | α | 90 |
| b | 18.51 ± 0.04 | β | 106.15 |
| c | 17.53 ± 0.04 | γ | 90 |

Unit cell volume: 5566.28 Å$^3$

The closeness of the values observed for the unit cell parameters is in agreement with the similarity in the powder diffractograms of the 2 compounds.

Thus, another subject-matter of the present invention is the tetrahydrate of the calcium or magnesium salt of irbesartan in the crystalline form.

In the examples which will follow, the following abbreviation HPLC is used for High Performance Liquid Chromatography.

EXAMPLE 1

Tetrahydrate of the Calcium Salt of Irbesartan 42.8 g of irbesartan are dissolved in a solution prepared from 4 g of sodium hydroxide in 430 ml of water. This solution is poured into a solution prepared from 11.1 g of calcium chloride in 500 ml of water. The reaction medium thus obtained is heated at 50° C. for 4 hours and is then allowed to return to ambient temperature. The salt obtained is filtered off, rinsed 3 times with 100 ml of water and then dried under vacuum at 50° C. to constant weight. 47.1 g of the expected salt are obtained.

The purity of the product is determined by HPLC to be 99.6%.

The analysis of the NMR (nuclear magnetic resonance) spectrum shows the absence of the peak corresponding to the proton of the tetrazole, the said peak being present in the NMR spectrum of the non-salified irbesartan.

The percentage analysis gives the following result:

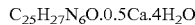

$C_{25}H_{27}N_6O.0.5Ca.4H_2O$

| | Theoretical | Found | |
|---|---|---|---|
| C | 57.80% | 56.60% | 56.42% |
| H | 6.74% | 6.66% | 6.63% |
| N | 16.18% | 15.81% | 15.78% |

The irbesartan content of the irbesartan salt, determined by HPLC, is 81.34% (theoretical: 82.26%).

The calcium content, determined by ionic HPLC, is 3.86% (theoretical: 3.90%).

Potentiometry shows 2 jumps equivalent to 40.83% and 39.04%; these jumps correspond to the theoretical expected value (82.26% in total).

Potentiometry makes it possible to quantify, by titrating the 2 basic functional groups of the said salt with perchloric acid, the amount of irbesartan present in the irbesartan salt.

The water content of the salt obtained is measured by the Karl-Fischer method (15.4%, i.e. 4H$_2$O) and by thermogravimetric analysis: thermogravimetric analysis makes it possible to measure the loss in weight at 100° C., that is to say the loss of water by weight: 12.96% i.e. 4 mol of water per mole of product.

The powder X-ray diffractogram recorded for the salt obtained is given in FIG. 1.

EXAMPLE 2

Tetrahydrate of the Magnesium Salt of Irbesartan 42.8 g of irbesartan are dissolved in a solution prepared from 4 g of sodium hydroxide in 430 ml of water. This solution is poured into a solution prepared from 9.52 g of magnesium chloride in 500 g of water. The reaction medium thus obtained is heated at 50° C. for 4 hours and is then allowed to return to ambient temperature. The salt obtained is filtered off, rinsed 3 times with 100 ml of water and then dried under vacuum at 50° C. to constant weight. 47.5 g of the expected salt are obtained.

The purity of the product is determined by HPLC to be 99.6%.

The analysis of the NMR (nuclear magnetic resonance) spectrum shows the absence of the peak corresponding to the proton of the tetrazole;

The percentage analysis gives the following result:

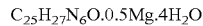

$C_{25}H_{27}N_6O.0.5Mg.4H_2O$

| | Theoretical | Found | |
|---|---|---|---|
| C | 58.71% | 57.45% | 57.26% |
| H | 6.85% | 6.78% | 6.77% |
| N | 16.43% | 16.06% | 16.03% |

The irbesartan content of the salt, determined by HPLC, is 82.39% (theoretical: 83.50%).

The magnesium content, determined by ionic HPLC, is 2.35% (theoretical: 2.87%).

Potentiometry shows 2 jumps equivalent to 41.29% and 88.12%.

The water content of the salt obtained is measured by Karl-Fischer (15.86%, i.e. 4H$_2$O) and thermogravimetric analysis: 12.26%, i.e. 4 mol of water per mole of product.

Figure 2:
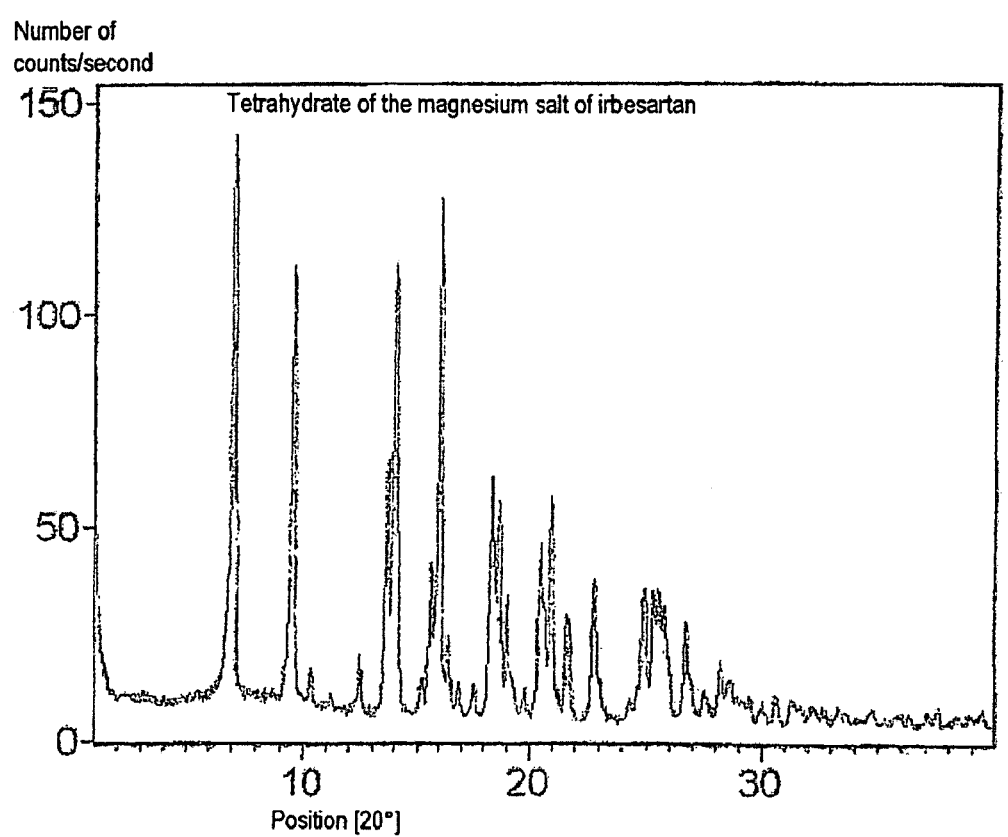
FIG. 2 shows the x-ray diffraction results for the tetrahydrate of the magnesium salt of irbesartan.

The powder X-ray diffractogram recorded for the salt obtained is given in FIG. 2.

What is claimed is:

1. A compound which is a hydrate of a pharmaceutically acceptable alkaline earth metal salt of irbesartan.

2. The compound according to claim 1, selected from a hydrate of the calcium salt of irbesartan, and a hydrate of the magnesium salt of irbesartan.

3. The compound according to claim 2, which is a tetrahydrate of the calcium salt of irbesartan.

4. The compound according to claim 2, which is a tetrahydrate of the magnesium salt of irbesartan.

5. The compound according to claim 3, wherein the compound is in a crystalline form.

6. The compound according to claim 4, wherein the compound is in a crystalline form.

7. A process for the preparation of an irbesartan salt hydrate according to claim 1, comprising:
   preparing a sodium salt of irbesartan in aqueous solution; and then
   displacing the sodium salt of irbesartan by the desired alkaline earth metal salt in aqueous medium.

* * * * *